United States Patent
Jeong

(10) Patent No.: US 8,053,201 B2
(45) Date of Patent: Nov. 8, 2011

(54) MICROFLUIDIC CONTROL CHIP AND METHOD OF DETECTING PROTEIN USING THE SAME

(75) Inventor: Min Suk Jeong, Jeongeup-si (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 12/861,694

(22) Filed: Aug. 23, 2010

(65) Prior Publication Data

US 2011/0129847 A1    Jun. 2, 2011

(30) Foreign Application Priority Data

Nov. 27, 2009    (KR) .................. 10-2009-0115740

(51) Int. Cl.
*G01N 33/53*    (2006.01)
(52) U.S. Cl. ......... 435/7.1; 435/325; 436/518; 436/520; 436/532; 436/546; 427/2.13
(58) Field of Classification Search ................. None
See application file for complete search history.

(56) References Cited

U.S. PATENT DOCUMENTS 7,108,993 B2    9/2006    Sommer et al.
2010/0261286 A1*  10/2010    Kim et al. .................. 436/149

FOREIGN PATENT DOCUMENTS

| EP | 0069869 | * | 1/1983 |
|---|---|---|---|
| JP | 2007-010341 | | 1/2007 |
| KR | 1020070106877 A | | 11/2007 |
| KR | 1020090006607 A | | 1/2009 |
| KR | 1020090064942 A | | 6/2009 |

OTHER PUBLICATIONS

Zhang et al., Biocompatibility evaluation of ePTFE membrane modified with PEG in atmospheric pressure glow discharge, 2002, J Biomedical Materials Research, 60(3): pp. 502-509.*
Susann Eriksson et al., "Negative Interference in Cardiac Troponin I Immunoassays by Circulating Troponin Autoantibodies", Proteomics and Protein Markers, 2005, pp. 839-847, vol. 51 No. 5, American Association for Clinical Chemistry.

* cited by examiner

*Primary Examiner* — N. C. Yang

(57) ABSTRACT

Provided is a microfluidic control chip, which includes a filter section having a filter to which anti-immunoglobulin antibodies, which are bound to endogenous antibodies in blood to thereby remove the endogenous antibodies, are immobilized, a first reaction section to which detection antibodies immobilized to fluorescent nano-particles are adsorbed, the detection antibodies being bound to proteins to be detected in blood which is introduced from the filter section with the endogenous antibodies removed therefrom, and a second reaction and detection section including capture antibodies immobilized thereto, binding the capture antibodies to the proteins, which are bound to the detection antibodies introduced from the first reaction section, and detecting a concentration of the proteins based on an intensity of fluorescent light. Thus, the microfluidic control chip can minimize interference of an immune response to maximize the immune response.

6 Claims, 3 Drawing Sheets

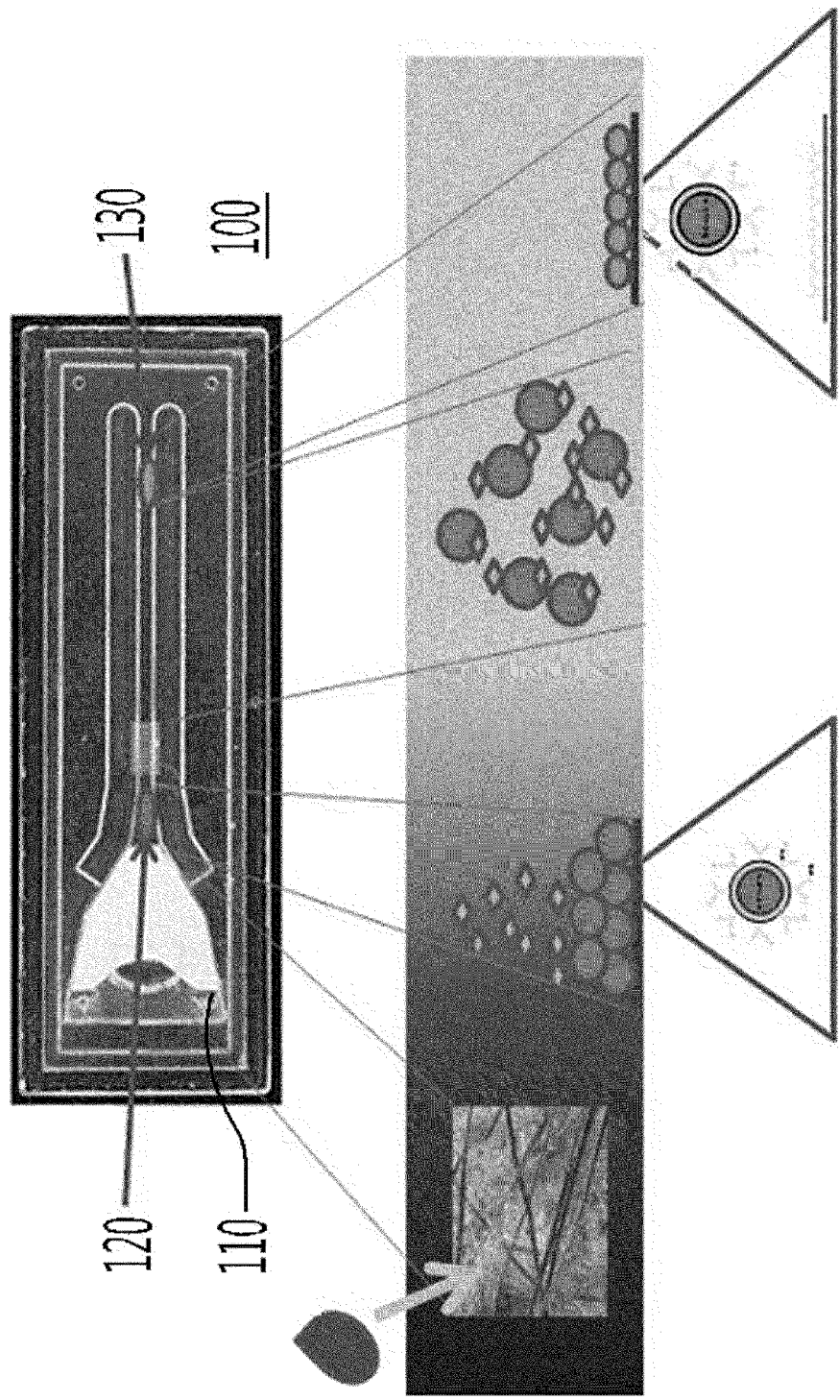

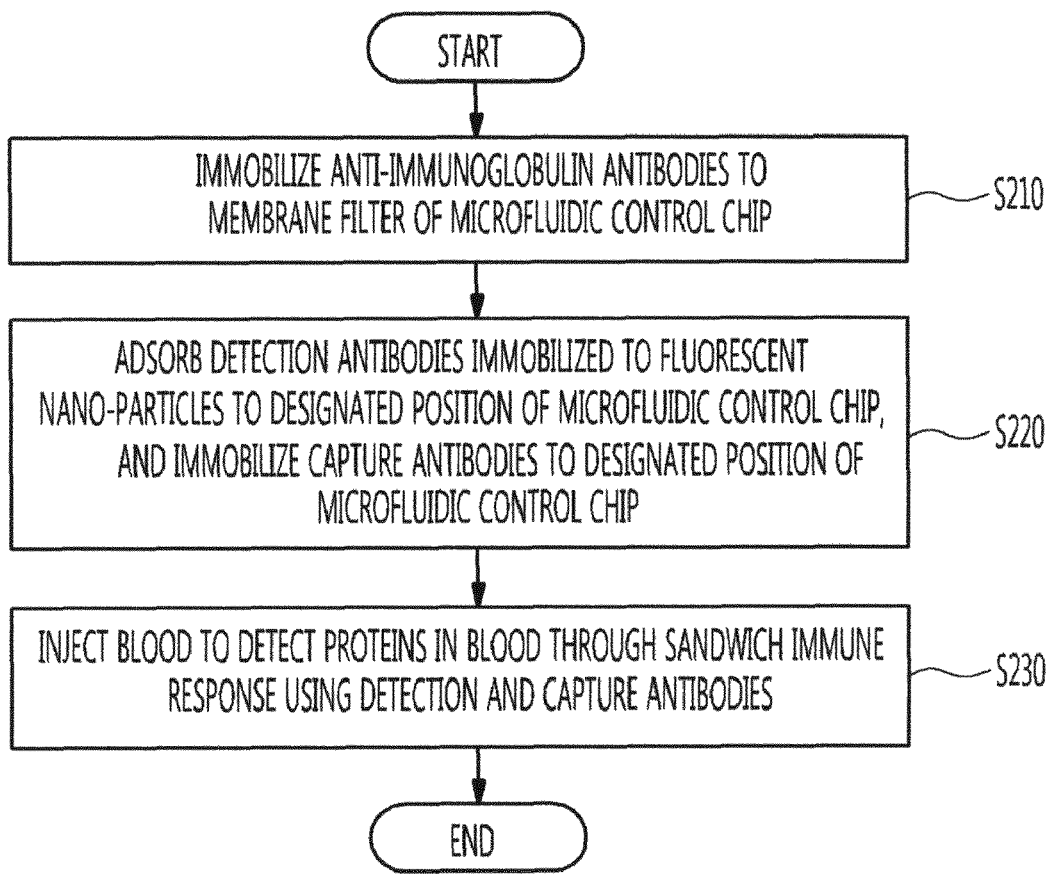

MICROFLUIDIC CONTROL CHIP AND METHOD OF DETECTING PROTEIN USING THE SAME

CROSS-REFERENCE TO RELATED APPLICATION

This application claims priority to and the benefit of Korean Patent Application No. 10-2009-0115740, filed Nov. 27, 2009, the disclosure of which is incorporated herein by reference in its entirety.

BACKGROUND

1. Field of the Invention

The present invention relates to a microfluidic control chip and, more particularly, to a microfluidic control chip capable of maximizing an immune response.

2. Discussion of Related Art

Recently, microfluidic control chips having a lab-on-a-chip type in which biochemical reactions such as biomarker detection of a specified disease from blood are integrally processed on a chip with minimum intervention of a tester have been frequently studied. Endogenous antibodies, such as heterophile antibodies, antianimal antibodies, autoantibodies, and therapeutic antibodies, which are present in the blood, hinder a sandwich immune response using specific binding between an antigen and an antibody, so that it is difficult to make an accurate diagnosis.

These endogenous antibodies which are present in the blood interfere with the immune response, thereby leading to a wrong diagnosis such as a false positive or negative diagnosis. To reduce the immune response intervention caused by these endogenous antibodies in the blood, a method of diluting a sample, removing interfering antibodies, or performing pre-treatment using a heterophilic blocking agent is used prior to testing. This method has a drawback in that a tester must make several tests, and it cannot be applied to all tests using the blood. In this process, there may occur a problem such as contamination of the blood.

SUMMARY OF THE INVENTION

The present invention is directed to a microfluidic control chip capable of removing endogenous antibodies in blood to thereby minimize interference of an immune response and maximizing the immune response, and a method of detecting proteins in blood using the same.

An aspect of the present invention provides a microfluidic control chip, which includes: a filter section having a filter to which anti-immunoglobulin antibodies, which are bound to endogenous antibodies in blood to thereby remove the endogenous antibodies, are immobilized; a first reaction section to which detection antibodies immobilized to fluorescent nano-particles are adsorbed, the detection antibodies being bound to proteins to be detected in blood which is introduced from the filter section with the endogenous antibodies removed therefrom; and a second reaction and detection section including capture antibodies immobilized thereto, binding the capture antibodies to the proteins, which are bound to the detection antibodies introduced from the first reaction section, and detecting a concentration of the proteins based on an intensity of fluorescent light.

In exemplary embodiments, the filter may be a membrane filter, which enables hemocytes and plasma to be separated from the blood.

In exemplary embodiments, the membrane filter may include a polymer, to which the anti-immunoglobulin antibodies are immobilized.

In exemplary embodiments, the polymer may include an immobilization part, a polyethylene glycol (PEG) part for preventing non-specific adsorption of the protein, and a functional group part for selectively immobilizing the antibody specific to the protein.

In exemplary embodiments, the anti-immunoglobulin antibodies may have a concentration of 100 μg/ml when immobilized.

In exemplary embodiments, the protein to be detected may be cardiac troponin I (cTnI).

Another aspect of the present invention provides a method of detecting proteins using a microfluidic control chip. The method includes: immobilizing anti-immunoglobulin antibodies to a filter of the microfluidic control chip, the anti-immunoglobulin antibodies being bound to endogenous antibodies in blood to remove the endogenous antibodies; adsorbing detection antibodies, which are immobilized to fluorescent nano-particles and are bound to the proteins to be detected, to a designated position of the microfluidic control chip when the blood from which the endogenous antibodies are removed is introduced; immobilizing capture antibodies, which are bound to the proteins bound to the detection antibodies to a designated position of the microfluidic control chip when the proteins bound to the detection antibodies are introduced; and injecting the blood into the microfluidic control chip to detect a concentration of the proteins based on an intensity of fluorescent light through a sequential immune response of the proteins in the blood from which the endogenous antibodies are removed, the detection antibodies immobilized to the fluorescent nano-particles, and the capture antibodies.

In exemplary embodiments, the filter may be a membrane filter, which enables hemocytes and plasma to be separated from the blood.

In exemplary embodiments, the membrane filter may remove the endogenous antibodies, as well as separate hemocytes and plasma from the blood at the same time.

In exemplary embodiments, the anti-immunoglobulin antibodies may be immobilized to a polymer included in the membrane filter.

In exemplary embodiments, the polymer may include an immobilization part, a polyethylene glycol (PEG) part for preventing non-specific adsorption of the protein, and a functional group part for selectively immobilizing the antibody specific to the protein.

In exemplary embodiments, the anti-immunoglobulin antibodies may have a concentration of 100 μg/ml when immobilized.

In exemplary embodiments, the protein to be detected may be cardiac troponin I (cTnI).

BRIEF DESCRIPTION OF THE DRAWINGS

The above and other features and advantages of the present invention will become more apparent to those of ordinary skill in the art by describing in detail preferred embodiments thereof with reference to the attached drawings in which:

FIG. 1 is a view explaining a microfluidic control chip according to an exemplary embodiment of the present invention;

FIG. 2 is a flowchart showing a method of detecting proteins in blood using a microfluidic control chip according to an exemplary embodiment of the present invention;

DETAILED DESCRIPTION OF EXEMPLARY EMBODIMENTS

Figure 3A:
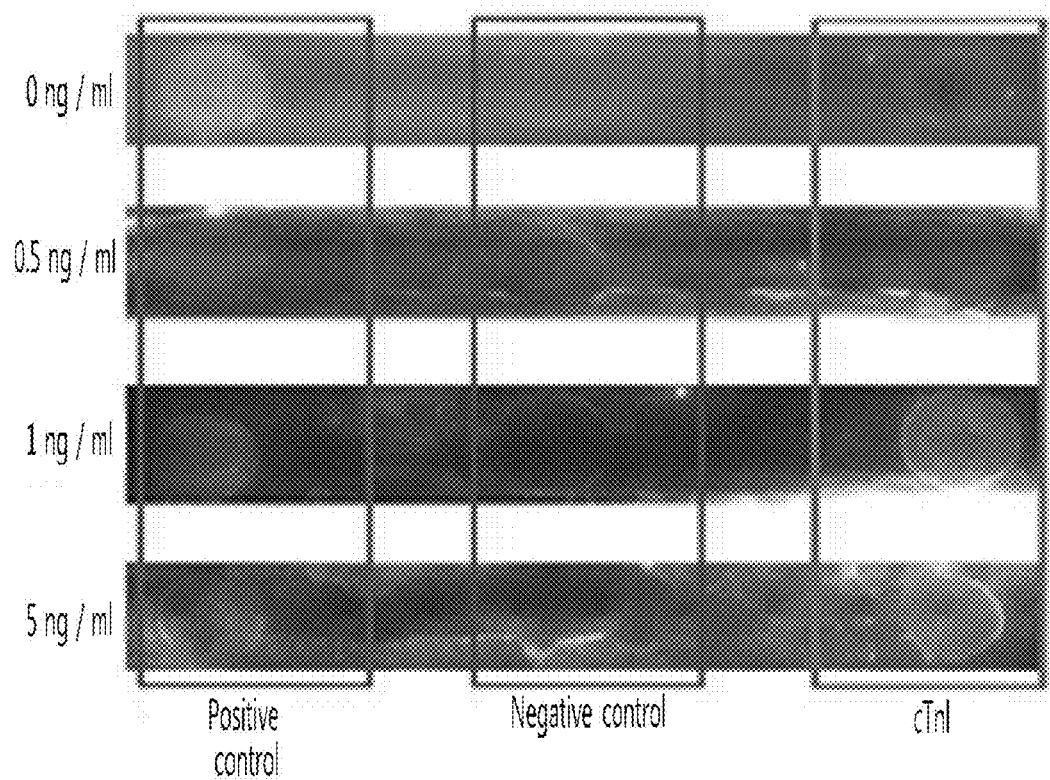
FIG. 3A shows a signal of fluorescent light of a sample from which endogenous antibodies are removed according to a concentration of cTnI.

The present invention will be described more fully hereinafter with reference to the accompanying drawings, in which exemplary embodiments of the invention are shown. This invention may, however, be embodied in different forms and should not be construed as limited to the embodiments set forth herein. In the following description of the present invention, a detailed description of known functions and components incorporated herein will be omitted when it may make the subject matter of the present invention rather unclear. It should be noted that the same reference numbers are used in the figures to denote the same elements.

It will be understood that, throughout the specification, unless explicitly described to the contrary, the term "comprise" and its conjugations such as "comprises" or comprising" should be interpreted to include stated elements but not exclude any other elements. In addition, the term "section," "device," or "module" used herein refers to a unit for processing at least one of a function and an operation, which can be realized by hardware, software, or a combination thereof.

FIG. 1 is a view explaining a microfluidic control chip according to an exemplary embodiment of the present invention.

A microfluidic control chip 100 according to an exemplary embodiment of the present invention includes a filter section 110, a first reaction section 120, and a second reaction and detection section 130.

The filter section 110 includes a filter to which anti-immunoglobulin antibodies are immobilized. These anti-immunoglobulin antibodies are bound to endogenous antibodies, thereby removing the endogenous antibodies.

Here, the filter may be a membrane filter that can separate hemocytes and plasma (or serum) from whole blood.

The membrane filter is originally used to separate the hemocytes and the plasma. However, in this embodiment, the membrane filter is used to remove the endogenous antibodies. As such, to check whether or not the immobilized anti-immunoglobulin antibodies capture and remove the endogenous antibodies, the plasma that has already separated from the whole blood is used without pre-treatment for separating the hemocytes and the plasma.

Alternatively, the pre-treatment for separating the hemocytes and the plasma may be performed, so that it is possible to separate the hemocytes and the plasma from the whole blood and simultaneously to remove the endogenous antibodies from the whole blood.

The membrane filter includes a polymer in order to immobilize the anti-immunoglobulin antibodies.

This polymer is immobilized to a hydrophobic surface through a covalent bond, and may immobilize biomolecules such as antibodies.

Further, the polymer is configured of an immobilization part, a polyethylene glycol (PEG) part for preventing non-specific adsorption of the biomolecule, and a functional group part for selectively immobilizing the biomolecule (or the antibody specific to a protein intended to be detected from the blood).

The anti-immunoglobulin antibody is immobilized to this polymer.

The first reaction section 120 includes detection antibodies, which are immobilized to fluorescent nano-particles and adsorbed thereto (wherein the detection antibodies are not chemically immobilized by a covalent bond, but physically adsorbed). When the blood from which the endogenous antibodies have been removed is introduced from the filter section 110, the detection antibodies are bound to the proteins (i.e. the biomarkers or antigens) to be detected from the blood (primary antigen-antibody reaction).

The second reaction and detection section 130 includes capture antibodies immobilized thereto. When the in-blood proteins (i.e. the biomarkers or antigens) bound to the detection antibodies are introduced from the first reaction section 120, the capture antibodies are bound to the in-blood protein (antigen)-detection antibody complexes (secondary antigen-antibody reaction). Thereby, the concentration of the proteins is detected by an intensity of fluorescent light.

Hereinafter, a method of detecting proteins in blood using the microfluidic control chip having the aforementioned configuration will be described.

FIG. 2 is a flowchart showing a method of detecting proteins in blood using a microfluidic control chip according to an exemplary embodiment of the present invention.

Referring to FIG. 2, first, anti-immunoglobulin antibodies are immobilized to the membrane filter (S210).

To this end, a polymer is pre-treated for one hour, and is cleaned with a citrate buffer of 50 mH (pH 3.3). The membrane filter after the pre-treatment of the polymer is treated with an anti-immunoglobulin antibody solution of 100 μg/ml for two hours such that the anti-immunoglobulin antibodies are immobilized, is cleaned several times with phosphate buffered saline (PBS) (pH 7.4), and is sufficiently dried in an oven. Thereby, the membrane filter to which the anti-immunoglobulin antibodies are immobilized is prepared.

Next, detection antibodies immobilized to fluorescent nano-particles are adsorbed to a designated position of the microfluidic control chip, and capture antibodies are immobilized to a designated position of the microfluidic control chip (S220).

The polymer is pre-treated on the surface of a plastic chip using the aforementioned method, and the capture antibodies are immobilized to the surface of the plastic chip.

In this embodiment, to detect cardiac troponin I (cTnI) from blood, cTnI antibodies having 1 mg/ml and available from Biodesign are used as the capture antibodies for immobilization.

The detection antibodies are immobilized to the surfaces of the fluorescent nano-particles by introducing an amine group into each fluorescent nano-particle by a reaction of sulfo-NHS and EDC according to a protocol provided by Invitrogen. The fluorescent nano-particles used for an immune response in this embodiment are 200 nm dark red fluorescent (660/680), into which carboxyl groups are introduced, available from Invitrogen. These fluorescent nano-particles are for increasing a quantity of the detection antibodies and an intensity of the fluorescent light.

Afterwards, blood is injected into the microfluidic control chip, and an in-blood protein to be detected is detected on the microfluidic control chip through a sandwich immune response using the capture antibodies and the detection antibodies (S230).

In this embodiment, the capture antibodies and the detection antibodies to which the fluorescent materials are adsorbed are used to detect the biomarker, cTnI, of acute myocardial infarction on the microfluidic control chip.

Through the resulting sandwich immune response, the concentration of cTnI in the blood is detected by the intensity of the fluorescent light.

However, the biomarker, cTnI, used in this embodiment is illustrative, and so the in-blood protein to be detected is not limited to this biomarker.

The microfluidic control chip is prepared by fitting the prepared membrane filter thereinto, immobilizing the detection and capture antibodies to respective designated positions, and bonding upper and lower plates using ultrasonic fusion. When this microfluidic control chip is prepared, 80 µl plasma solutions in which the cTnI antigens are diluted for testing according to concentration are each injected onto the microfluidic control chip.

While the plasma solution is passing through the membrane filter of the filter section, the endogenous antibodies are removed. Then, the remaining antigens are bound to the detection antibodies immobilized to the fluorescent nano-particles (or the fluorescent materials) first, thereby making a primary antigen-antibody reaction (that is, when the blood is injected, and then the parts where the detection antibodies of the microfluidic control chip are adsorbed are dissolved, the antigens in the blood from which the endogenous antibodies are removed are bound to the detection antibodies immobilized to fluorescent nano-particles for the antigen-antibody reaction).

Afterwards, the capture antibodies are again bound to the antigen-detection antibody complexes at the portion where the capture antibodies are immobilized for a secondary antigen-antibody reaction as a sandwich immune response. Through the reaction, the concentration of cTnI is detected by the intensity of the fluorescent light (that is, since the capture antibodies are immobilized to the designated position of the microfluidic control chip, a degree to which the capture antibodies are again bound to the antigen-detection antibody complexes can be detected by the intensity of the fluorescent light.

Figure 3B:
FIG. 3B shows a signal of fluorescent light of a sample from which endogenous antibodies are not removed according to a concentration of cTnI.

FIG. 3A shows a signal of fluorescent light of a sample from which endogenous antibodies are removed according to a concentration of cTnI, and FIG. 3B shows a signal of fluorescent light of a sample from which endogenous antibodies are not removed according to a concentration of cTnI.

Referring to FIGS. 3A and 3B, it can be found that the signal of fluorescent light of the sample from which the endogenous antibodies are removed is much clearer than the signal of fluorescent light of the sample from which the endogenous antibodies are not removed.

Further, in the case of a negative control (group), it can be found that the fluorescent signal is hardly represented.

In this embodiment, the signal of fluorescent light of the sample according to the concentration of cTnI is similar to, and rather much clearer than, that of a positive control. It can be found from this phenomenon that the method of detecting proteins in blood using a microfluidic control chip according to an exemplary embodiment of the present invention can effectively detect cTnI.

According to exemplary embodiments, a microfluidic control chip (or biochip) for detecting the proteins from the blood can maximize the immune response using its membrane filter to which the anti-immunoglobulin antibodies are immobilized.

Further, the microfluidic control chip can be simply manufactured using a method of immobilizing the anti-immunoglobulin antibodies to its membrane filter, and can be applied to various lab-on-a-chips such as protein chips, micro biochemical analysis systems, micro biochemical reactors, and so on.

A method of detecting proteins using the microfluidic control chip can automatically and precisely detect the proteins from the blood without interference of the endogenous antibodies by simply injecting a predetermined quantity of blood of a testee onto the microfluidic control chip.

The exemplary embodiments of the present invention described above can be implemented not only by the apparatus and/or method, but also by a program that achieves the function corresponding to the configuration of the exemplary embodiments of the present invention or a recording media on which the program is recorded. This will be easily implemented from the disclosure of the aforementioned exemplary embodiments of the present invention by those skilled in the art.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method of detecting proteins using a microfluidic control chip, comprising:
   immobilizing anti-immunoglobulin antibodies to a membrane filter of the microfluidic control chip;
   injecting blood into the chip;
   binding endogenous antibodies in the blood to the anti-immunoglobulin antibodies while simultaneously separating hemocytes and plasma from the blood with the membrane filter; coupling detection antibodies to fluorescent nano-particles; adsorbing the detection antibodies to a detection antibodies portion of the microfluidic control chip;
   immobilizing capture antibodies to a capture antibodies portion of the chip;
   dissolving the detection antibodies into the blood;
   binding the detection antibodies to the proteins to be detected in the blood;
   conveying the detection antibodies from the detection antibodies portion of the chip to a capture antibodies portion of the chip;
   binding the proteins to the capture antibodies;
   detecting an intensity of fluorescent light emitted from the capture antibodies portion of the chip; and
   determining a concentration of the proteins in the blood based on the intensity of fluorescent light.

2. The method according to claim 1, wherein the anti-immunoglobulin antibodies are immobilized to a polymer included in the membrane filter.

3. The method according to claim 2, wherein the polymer includes an immobilization part configured to immobilize the polymer to the membrane filter, a repellent part for preventing non-specific adsorption of the protein, and a functional group part for selectively immobilizing the anti-immunoglobulin antibody.

4. The method according to claim 1, wherein the anti-immunoglobulin antibodies are immobilized from a solution with a concentration of 100 µg/ml.

5. The method according to claim 1, wherein the protein to be detected is cardiac troponin I (cTnI).

6. The method according to claim 3, wherein the repellent part includes polyethylene glycol (PEG).

* * * * *